(12) United States Patent
Amara et al.

(10) Patent No.: US 8,700,171 B2
(45) Date of Patent: Apr. 15, 2014

(54) CONTROLLED SWITCHING MODULE FOR A MULTIELECTRODE LEAD FOR AN ACTIVE IMPLANTABLE MEDICAL DEVICE

(71) Applicant: Sorin CRM S.A.S., Clamart (FR)

(72) Inventors: Karima Amara, Sceaux (FR); Islam Seoudi, Chatenay Malabry (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 13/651,591

(22) Filed: Oct. 15, 2012

(65) Prior Publication Data

US 2013/0096647 A1 Apr. 18, 2013

(30) Foreign Application Priority Data

Oct. 13, 2011 (FR) ...................... 11 59288

(51) Int. Cl.
*A61N 1/00* (2006.01)
(52) U.S. Cl.
USPC ............................................................ 607/59
(58) Field of Classification Search
USPC ............................................................ 607/59
See application file for complete search history.

(56) References Cited

U.S. PATENT DOCUMENTS

| | | | |
|---|---|---|---|
| 2007/0203547 A1* | 8/2007 | Costello et al. ................ | 607/59 |
| 2008/0177343 A1 | 7/2008 | Dal Molin et al. | |
| 2009/0118790 A1 | 5/2009 | Van Herk | |
| 2009/0192572 A1 | 7/2009 | Dal Molin et al. | |
| 2009/0198313 A1 | 8/2009 | Doerr | |
| 2009/0310268 A1 | 12/2009 | Bertin et al. | |
| 2010/0312298 A1 | 12/2010 | Pontiga et al. | |
| 2011/0029042 A1 | 2/2011 | Malinowski et al. | |

FOREIGN PATENT DOCUMENTS

| | | |
|---|---|---|
| EP | 1938861 A1 | 7/2008 |
| EP | 2082684 A1 | 7/2009 |

OTHER PUBLICATIONS

Foreign Search Report (Annexe Au Rapport De Recherche Preliminaire Relatif A La Demande De Brevet Francais No. FR 1159288 FA 755996), Mar. 6, 2012.

* cited by examiner

*Primary Examiner* — Robert N Wieland
(74) *Attorney, Agent, or Firm* — Foley & Lardner LLP

(57) ABSTRACT

A controlled switching module (40, 42), for a multielectrode lead for an active implantable medical device, which connects a detection/stimulation electrode (28, 30) to one or the other conductor (36, 38) of a two-wire line. Two volatile controlled switches (52, 54), for example, complementary MOS associated with at least one non-volatile programmable memory component (68, 70), for example, a suspended nanotube cell or a magnetic tunnel junction cell, supply two previously programmed stable open or closed states. A generator maximum-minimum circuit (58) is coupled to the conductors at the input, and to the controlled switches at the output for selectively controlling them via the corresponding non-volatile memory component (68, 70).

17 Claims, 2 Drawing Sheets

Figure 3:
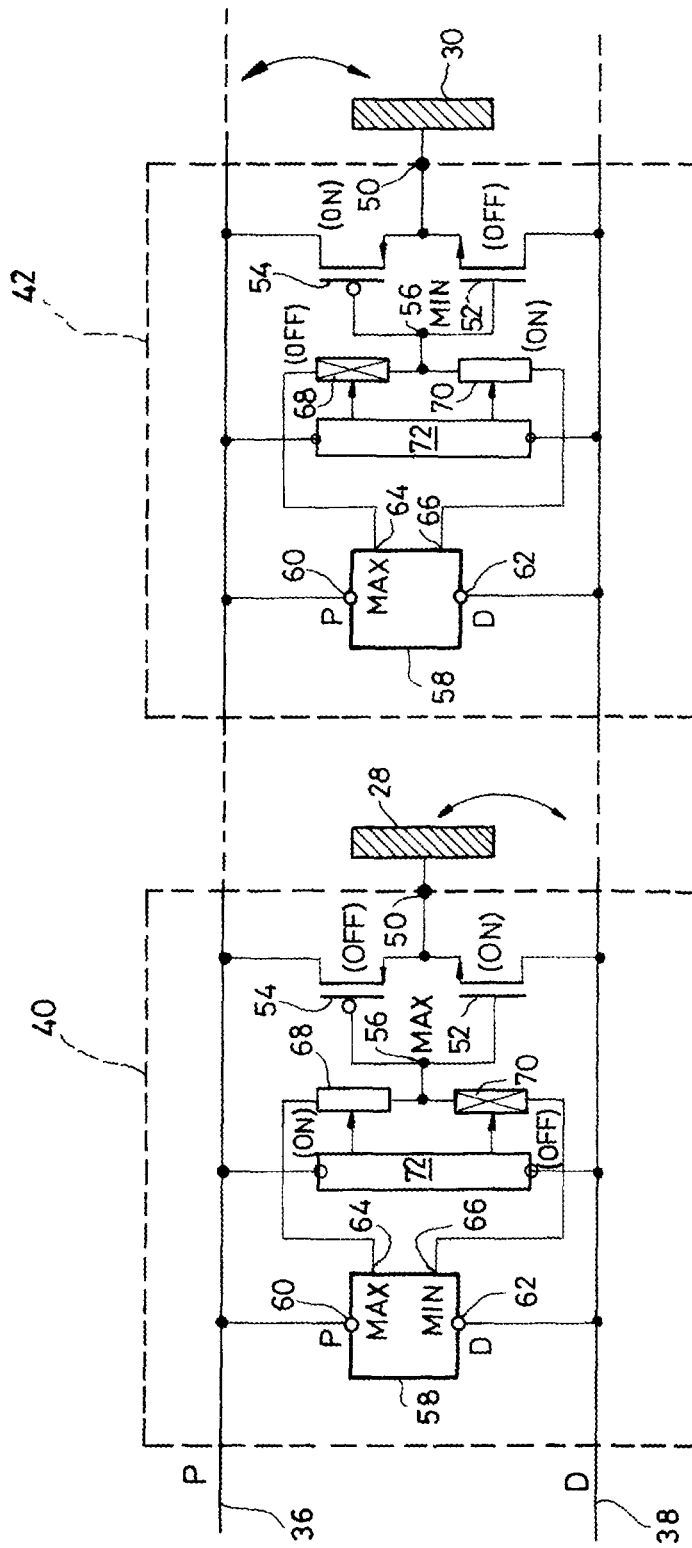

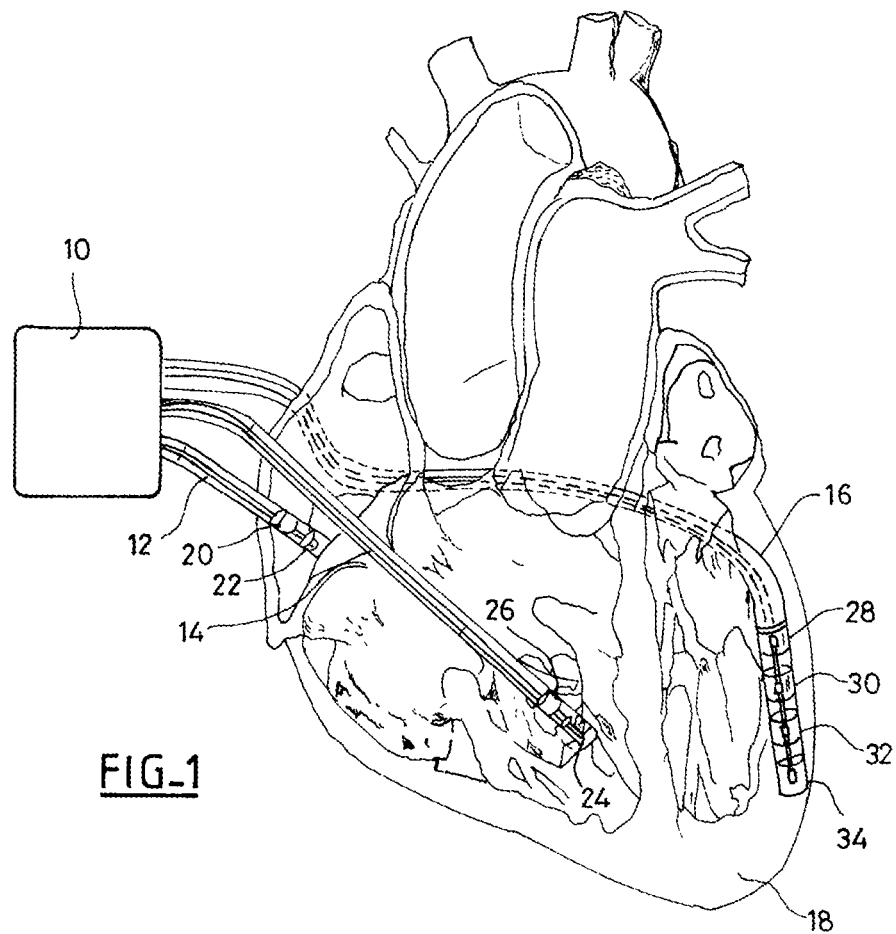
FIG_1
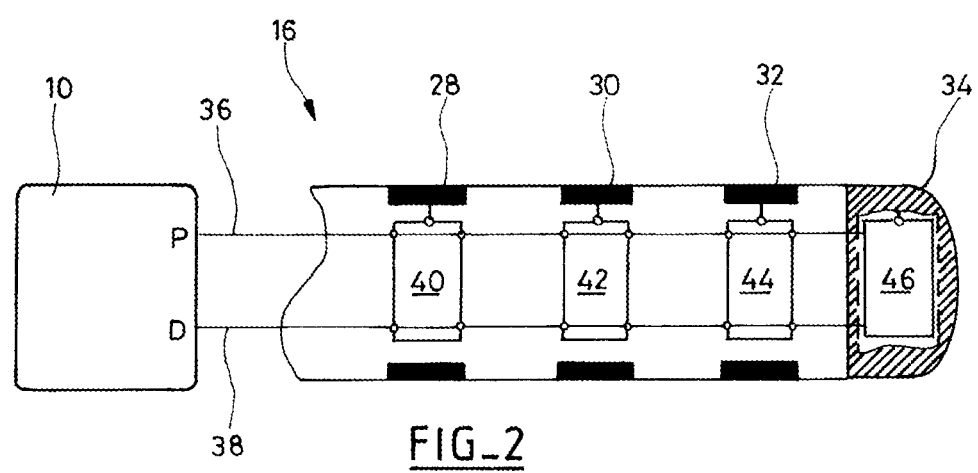
FIG_2

CONTROLLED SWITCHING MODULE FOR A MULTIELECTRODE LEAD FOR AN ACTIVE IMPLANTABLE MEDICAL DEVICE

RELATED APPLICATION

The present application claims the priority date benefit of French Patent Application No. 11/59288 entitled "Controlled switching module for a multielectrode lead for an active implantable medical device", and filed Oct. 13, 2011.

FIELD OF THE INVENTION

The present invention relates to "medical devices" as defined by the Jun. 14, 1993 directive 93/42/CE of the European Community Council, and more particularly to "active implantable medical devices" as defined by the Jun. 20, 1990 directive 90/395/CEE of the European Community Council. These devices include in particular apparatus for monitoring a patient's cardiac activity and generating electrical pulses for stimulation, resynchronization, defibrillation and/or cardioversion, in response to an arrhythmia detected by the device, as well as neurological devices, pumps for diffusion of medical substances, cochlear implants, implanted biological sensors, etc., and devices for measuring pH or intracorporeal impedance (such as transpulmonary impedance measurement or intracardiac impedance) and to mulitelectrode lead devices to be coupled to such medical devices.

BACKGROUND

These medical devices typically comprise a housing that is generally designated a "generator", which is electrically and mechanically connected to one or more other devices known as "leads". Leads are provided with electrodes that are intended to come into contact with the patient's tissues at sites to stimulate (i.e., deliver electrical pulses to the tissues) and/or at which it is desired to collect (i.e., sense, detect) an electrical signal. Such sites include, but are not limited to a patient's myocardium, nerve, or muscle tissue. In the case of a diagnostic and therapeutic cardiac device, the electrodes can be endocardial electrodes (e.g., placed in a cavity of the myocardium in contact with the wall thereof), epicardial electrodes (used in particular to define a reference potential, or for application of a shock pulse used for defibrillation), or intravascular electrodes (for example, the lead is introduced into the coronary sinus to a location facing the wall of the left ventricle).

One aspect of the development of these devices is the increasing number of electrodes employed in a lead, especially for those devices known as "multisite" devices that allow selection of the stimulation/detection sites for optimization of the operation of the device.

Thus, in the particular case of implantable devices used for ventricular resynchronization (which devices also are called cardiac resynchronization therapy (CRT) devices), a patient is implanted with a device having electrodes to stimulate either or both ventricles. The right ventricular pacing (and the right atrium pacing) is typically obtained using a conventional endocardial lead, but for the left ventricle the access is more complex; stimulation is generally performed using a lead that is inserted into the coronary sinus of the right ventricle and then pushed into a coronary vein on the epicardium, so that the end of the lead comes into contact with and against the left ventricle. This procedure is quite delicate, because the diameter of coronary vessels is reduced as the lead progresses, so it is not always easy to find the optimal position during implantation. In addition, the proximity of the phrenic nerve can sometimes lead to inappropriate stimuli.

To alleviate these difficulties, efforts were conducted to develop "multielectrode" leads, providing, for example, several electrodes among which the most effective stimulation electrode configuration can be tested and then chosen after implantation. One such lead is described for example in EP 1938861 A1 and its counterpart U.S. Pat. Publication No. 2008/0177343 A1 (both assigned to Sorin CRM S.A.S, previously known as ELA Medical).

To manage a multiplicity of electrodes, multiplexing systems for interfacing the various electrodes (and any sensors carried by the lead) have been developed with the two conductors traversing the lead and connected to the generator terminals. EP 2082684 A1 and its counterpart U.S. Pat. Publication No. 2009/0192572 A1 (both assigned to Sorin CRM S.A.S, previously known as ELA Medical) describe a generator connected to a multielectrode lead by two conductors associated with a multiplexor/demultiplexor circuit. The two conductors firstly ensure the collection of depolarization signals and the delivery of stimulation pulses, and secondly deliver the multiplexor/demultiplexor logic signals to control the selector switches of one or more electrodes of the lead. These signals also supply the required energy to the multiplexor/demultiplexor circuit and switches for their operation. Aforementioned EP 1938861 A1 and its counterpart U.S. Pat. Publication No. 2008/0177343 A1 describe such a multiplexor and controlled switching circuit, and a protocol for exchanging signals between the generator and the various multiplexors of the lead to ensure the desired switching by delivering trains of pulses on the specific two-wire line.

The U.S. Pat. Publication 2011/0029042 A1 describes another device comprising a controlled switch module of the same type, with a controlled switch associated with a memory component that stores a unique identifier used for addressing by the multiplexor/demultiplexor.

A first drawback of these known devices is the need to provide a permanent power supply to the circuits that allow the multiplexing of the switches defining the electrode configuration. This results in an increase in overall implant/lead system power consumption, which is detrimental to the autonomy (i.e., the useful life) of an implanted device.

Specifically, for a given multielectrode lead as described in the above two patent publication documents, the electrodes are selected by the generator via the two-wire link carried by the lead body, whose two poles are generally designated as "distal" and "proximal" poles. Note that in some cases, the link can include one or more additional conductors, and the connection may, for example, be a three wire connection incorporating an additional conductor for direct transmission to the generator of signals produced, for example, by an endocardial acceleration sensor located in the lead distal tip.

A circuit module, generally formed as a specific integrated ASIC circuit, is integrated at each electrode. This module, which must be supplied via the two-wire connection, receives the configuration data to define if the corresponding electrode has to be connected or not and, if so, to which pole, the distal or proximal one. The configuration data are interpreted by the module, which performs (or not) the connection of one or the other of the distal or proximal conductors to the selected electrode by means of controlled switches.

These controlled switches are generally volatile switches, usually MOS transistors or MEMS, which are easy to implement. However, once the various modules of the lead are configured to activate one or more stimulation sites corresponding to the respective electrodes, the electrode configuration must be continuously maintained for the collection of the cardiac signal and the delivery, if necessary, of stimulation pulses.

One drawback is the need to permanently or periodically provide sufficient energy (that is to say, at least throughout the period when the device is active) to supply the different modules of the lead. Another drawback is that for a given lead, it is necessary to use a specific implantable medical device which is dedicated to the particular lead. Indeed, the generator associated with the lead must be able to provide the appropriate signals to control the multiplexing and the energy to make and keep the lead functional. Yet another drawback is that in some cases the lead is no longer supplied with power by the generator, resulting in a loss of the pacing configuration, which must be reprogrammed. This is particularly true at the end of life of the implant (i.e., a low battery condition), during replacement of the original implantable device with a new implantable device: during surgery, the lead is de-energized and once the new implant able device is in place and coupled to energize the lead it is necessary to reconfigure the lead electrodes to their previous state—which in addition assumes that the previous state was saved while the old generator was still functional.

OBJECTS AND SUMMARY

It is, therefore, an object of the present invention to reduce the energy consumption of a multielectrode lead system, where energy consumption is related to the supply of power to the modules to maintain the electrodes of the lead in the optimal configuration chosen.

It is another object of the present invention to overcome the need for reprogramming of the switched electrode configuration in the event of a generator change, e.g., maintaining the configuration even in the absence of a power supply to the lead.

It is yet another object of the present invention to provide compatibility between any generator and any multielectrode lead. From the generator side, it is making the lead appear equivalent to an industry standard lead, preferably a bipolar lead and thus compatible with generators of different models or brands, as long as it meets, for example, the IS-1 connection standards (for a simple bipolar configuration). Adapting the multielectrode configuration is then carried out by the lead itself—and not by the generator, which can be devoid of multiplexing functions to the extent that the lead retains the electrode configuration as initially defined.

In other words, the present invention is directed to reduce energy consumption and to make a multielectrode lead compatible with any type of industry standard meeting generator on the market, guaranteeing a bipolar or unipolar connection identical to the last electrode configuration chosen before the replacement of the generator that allowed the initial programming of the configuration of electrodes of the lead.

Broadly, the present invention is directed to an improved module for controlling switching of multiple electrodes of the type disclosed in U.S. Pat. Publication No. 2011/0029042 A1 cited above, which disclosure is hereby incorporated herein by reference, for an active implantable medical device comprising a generator and a lead connected to the generator and provided with a plurality of detection/stimulation selectively switchable electrodes.

In one embodiment, the module comprises: at least one proximal terminal and at least one distal terminal connected to the generator, each terminal being able to be coupled to respective conductors of a two-wire line of the lead; an electrode terminal connected to one of the detection/stimulation electrodes of the lead, a selective switching circuit for selectively switching the electrode terminal to connect to one or the other of the proximal and distal terminals, comprising at least one controlled switch respectively coupling the electrode terminal to the proximal terminal and the distal terminal and at least one programmable non-volatile memory component associated with at least one controlled switch; a power supply for operating the active circuitry; and a decoding circuit of the signals supplied by the generator and transmitted by the two-wire line for controlling the selective switching circuit according to a corresponding particular configuration.

In a preferred embodiment, there are two controlled switches, each having an associated non-volatile programmable memory component and respectively coupling the electrode terminal to the proximal and distal terminals. Each controlled switch is a volatile switch requiring a power supply for activation and stability. The non-volatile programmable memory component has in the absence of a power supply two stable states, one stable state controlling a corresponding open state of the controlled switch and the other stable state controlling a corresponding closed state of the controlled switch. The decoding circuit comprises means for previously programming the state of the non-volatile programmable memory by corresponding signals applied by the generator on the two-wire line. The switching circuit further comprises a maximum-minimum generator circuit having a maximum voltage output and a minimum voltage output, coupled between the proximal and distal terminals and coupled at the outputs to the controlled switches for selectively controlling the switches via the corresponding non-volatile programmable memory component.

In one preferred embodiment, the two controlled switches are complementary switches controlled by the application of a voltage to a common controlling terminal, so that when one of the switches is controlled open the other switch is controlled closed, and vice versa. In this embodiment, the module may comprise two non-volatile memory components connected in series between the minimum output and the maximum output of the maximum-minimum generator. One of the non-volatile programmable memory components is programmed into one of its stable states and the other is programmed into the other stable state. The midpoint of the series circuit is connected to the common controlling terminal of the complementary switches.

In one embodiment, the non-volatile programmable memory component can in particular be a suspended nanotube cell, or a magnetic tunnel junction cell.

Another aspect of the present invention relates to a lead, incorporating a module for controlled switching of electrodes as described above.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 1 schematically illustrates an example of a medical device comprising a generator and three leads implanted in three respective myocardium cavities of a human patient;

FIG. 2 illustrates modules in accordance with a preferred embodiment of the present invention coupled to a two-wire connection between the generator and the distal end of one of the leads of the system of FIG. 1, with the respective switchable electrodes; and FIG. 3 is a circuit schematic of the various components and functional blocks of two of the modules schematically shown in FIG. 2.

DETAILED DESCRIPTION

A non limitative example of implementation of a preferred embodiment of the present invention will now be described with reference to the drawing FIGS. 1-3.

In FIG. 1, reference 10 designates a generator housing of an active implantable medical device such as a defibrillator, pacemaker or resynchronizer device. This application is in no way limitative, however, because the present invention is applicable to other medical devices such as nerve or muscle detection/stimulation implants, etc.

Generator 10 is associated with three distinct leads 12, 14 and 16, each having a distal end located in a different location of the patient's myocardium 18. Lead 12 is, for example, an atrial endocardial lead having at its distal end two switches for selecting a corresponding stimulation electrode 20 or 22.

Lead 14 is an endocardial lead implanted in the ventricle, which includes at its distal end two switches for the selection of an electrode 24 or 26. Lead 16 is a coronary lead used for stimulation of the left heart cavities, which includes at its distal end, for example, four switches for the selection of four respective stimulation electrodes 28, 30, 32 and 34. These various leads may also include various sensors (not shown in the figures), in particular for measuring an endocardial acceleration.

The distal end tip of lead 16, with the understanding that the other two leads 12 and 14 may be configured similarly, is shown in more detail in FIG. 2. Lead 16 includes two connecting conductors in the form of microcables 36, 38 which run along its entire length and are connected to generator 10. Conductors 36 and 38 are respectively referred to as "proximal microcable" 36 and "distal microcable" 38, and the corresponding terminals of the generator are designated as "distal" and "proximal", by analogy with the relative positioning of two electrodes along a single endocardial bipolar lead.

Proximal microcable 36 and distal microcable 38 are connected to a set of modules 40, 42, 44, 46, disposed in lead 16 at the respective electrodes 28, 30, 32, 34. Modules 40, 42, 44, 46 may preferably be ASIC devices, whose internal functional structure is described in detail with reference to FIG. 3. Modules 40, 42, 44, 46 are coupled to microcables 36 and 38 in the manner of a bus, with each module respectively managing the connection of the electrode 28, 30, 32, 34 to which it is associated with one or the other of the microcables 36 or 38 (or neither), so as to define a stimulation configuration according to the desired switch configuration.

Thus, in the embodiment of a bipolar stimulation condition, some electrodes 28, 30, 32, 34 are connected to the proximal microcable 36, while the other(s) are connected to the distal microcable 38 (or if the electrode is not selected, it is not connected to either microcable). It is also possible to have only monopolar stimulation, by switching some (or all) of the electrodes to only one of the microcables 36 or 38, the other pole of stimulation consisting of the metal housing of generator 10.

The various modules 40, 42, 44, 46 are preferably identical and differ only by their multiplexing address, as is necessary for their identification at the time of initial programming of the pacing configuration.

FIG. 3 illustrates in greater detail two of these modules, such as modules 40 and 42 associated with electrodes 28 and 30. It should be understood that in the illustrated example each module is associated with a single electrode, but one can envision a configuration in which several electrodes are switched simultaneously by the same module, and hence the configuration shown is not considered exhaustive.

The electrode (28, 30) is connected to a terminal electrode 50 of the module (40, 42), which is also connected to the proximal microcable 36 and distal microcable 38 by corresponding terminals. Hence, electrode 28, via terminal 50, can alternately be connected to one or the other of microcables 36 or 38 via controlled switches 52 and 54, for example, MOS or MEMS switches. In the illustrated example, controlled switches 52, 54, are complementary MOS whose control electrodes are connected to a common point 56. The configuration has two states according to the voltage at node 56:

(i) For a high voltage at point 56, switch 52 is ON and switch 54 is OFF, so that electrode 28 is then placed to the potential of distal microcable 38; and (ii) For a low voltage at point 56, the configuration is reversed: switch 52 is OFF, switch 54 is ON, and electrode 28 is then placed to the potential of the proximal microcable 36.

Activation of controlled switches 52, 54, is achieved through a circuit 58 which is a maximum/minimum generator (MMG). The input of MMG circuit 58 is connected to proximal microcable 36 via terminal 60 and to distal microcable 38 via terminal 62. MMG circuit 58 outputs, on terminal 64, a maximum value of the voltage applied between the proximal microcable 36 and distal microcable 58, and on terminal 66, the minimum voltage applied between these same microcables.

MMG circuit 58 is coupled to controlled switches 52 and 54 through non-volatile programmable memory components 68 and 70. Components 68, 70 can take one of two states according to their programming, and maintain that state even without power. The non-volatile programmable memory components used in the context of the present invention may, for example, be suspended nanotube cells as described for example in U.S. Pat. Publication No. 2009/0310268 A1, the disclosure of which is incorporated herein by reference. It may also be magnetic tunnel junction (MTJ) cells, which are known cells comprising a very thin layer of an insulating or semiconductor material sandwiched between two ferromagnetic layers: if a potential difference is applied between the two ferromagnetic layers, a current flows through the insulating layer, also called the tunnel barrier; the resistance value of the junction, according to quantum effects, can take two extreme values depending on the parallel or anti-parallel configuration of magnetization of the ferromagnetic layers. The magnetic tunnel junction is a well known technology in the field of nonvolatile memories, e.g., from companies like EVERSPIN and CROCUS Technology among others.

Regardless of the chosen technology for non-volatile programmable memory components 68, 70, they have two stable states, with a low resistance "closed" state (also referred to as a passing state or ON), and a high resistance "open" state (also referred to as a blocking state or OFF). One state or the other is predefined by a programming circuit 72 based on specific programming pulses applied to microcables 36 and 38, for example, signals such as those described in EP 1938861 A1 cited above.

The essential characteristic of non-volatile programmable memory components 68, 70 is that they are not volatile, that is to say, after they have been programmed, they permanently retain their status and assigned state without requiring any power.

In the case of the modules illustrated in FIG. 3, the two components 68, 70 are programmed so that their respective states are opposites: one is closed when the other is open, or vice versa. For example, for module 40, component 68 is closed and component 70 is open, while for module 42, component 68 is open and component 70 is closed.

These non-volatile programmable memory components are inserted:

For component 68, between maximum output terminal 64 of MMG circuit 58, on the one hand, and midpoint 56 of the control electrodes of complementary MOS 52, 54, on the other; and For component 70: between minimum output terminal 66 of MMG circuit 58, on the one hand, and midpoint 56 of the control electrodes of complementary MOS 52, 54, on the other.

With reference to the example illustrated in FIG. 3, for module 40 wherein non-volatile programmable memory component 68 is programmed on, it is the maximum voltage, present on terminal 64, which is applied at midpoint 56 of control MOS 52, 54, which have the effect of turning on MOS 52 and off (complementary) MOS 54.

For switching module 42, the situation is reversed: the fact that non-volatile programmable memory component 70 is on means that it is the minimum voltage at terminal 66 which is applied to control electrodes of the MOS 52, 54, turning on the (inverted) MOS 54 and off the MOS 52.

Thus, electrode 30 is at the potential of proximal microcable 36, while electrode 28 is at the potential of distal electrode 38. Bipolar pacing between two electrodes 28 and 30 (and similarly with the other electrodes of the lead that may be present) can be obtained with this configuration, by combining, according to the invention, (i) volatile controlled switches (MOS 52, 54) with (ii) non-volatile programmable memory components (68, 70).

The absence of power on the lead, for example, when replacing the lead or the generator, does not result in deprogramming the switch configuration. Nor does the lead have to be reprogrammed with the prior switched electrode configuration, for example, after an exchange or disconnection of the generator.

For a multielectrode lead, it is possible to connect any of the electrodes either to the proximal terminal or at the distal terminal of the generator, which then provides a very large number of possible configurations and therefore greater flexibility for improved therapy of the patient. Advantageously, once a configuration has been set and programmed, it is no longer required to periodically reconfigure the modules, or maintain their power.

Note also that, advantageously, the current through the cells of non-volatile programmable memory components 68, 70 is a low current, which allows the use of technologies such as those mentioned above of suspended nanotube cells or magnetic tunnel junction cells, which support only a very low current. The stimulation current itself does not pass through these memory cells, but through the MOS controlled switches 52, 54, whose resistance $R_{on}$ in the closed state is low. The current that may be delivered is thus not limited by the chosen switching technology, and moreover, because of the low resistance $R_{on}$ in the ON state, the impedance seen from the generator is not significantly altered.

Advantageously, it should be understood that stimulation can in no case de-program or destroy the non-volatile programmable memory components 68, 70 so that it is not necessary to take special protective measures for them.

One skilled in the art will appreciate that the present invention can be practiced by embodiments other than those described herein, which are provided for purposes of explanation, and not of limitation.

The invention claimed is:

1. An electrode controlled switching module, for an active implantable medical device having a generator, a lead having a two-wire line connected to said generator, and a plurality of selectively switchable detection/stimulation electrodes, said module comprising:

At least one proximal terminal and at least one distal terminal for coupling to respective conductors of a two-wire line of the lead connected to the generator;

An electrode terminal, connected to one of said detection/stimulation electrodes of the lead;

A first circuit for selectively switching the electrode terminal to one or other of the proximal and distal terminals, said first circuit comprising a first controlled switch and a second controlled switch respectively coupling the electrode terminal to the proximal and distal terminals, said first and second controlled switches being volatile switches requiring activation by a power supply, and a first non-volatile programmable memory component associated with said first controlled switch and a second non-volatile programmable memory component associated with said second controlled switch, each of said non-volatile programmable memory components having in the absence of a power supply at least two stable states, one of said stable states controlling a corresponding open state of its associated controlled switch and the other of said stable states controlling a corresponding closed state of its associated controlled switch, and a maximum-minimum generator (MMG) circuit, having an input, a maximum output and a minimum output, coupled at the input between the proximal and distal terminals and coupled at the maximum and minimum outputs to the first and second controlled switches for selectively controlling them via the corresponding non-volatile programmable memory component, wherein the first non-volatile programmable memory component and the second non-volatile programmable memory component are configured to control states of the first controlled switch and the second controlled switch, respectively, to control whether the electrode terminal is connected to the proximal terminal or the distal terminal, and wherein the first non-volatile programmable memory component and the second non-volatile programmable memory component are configured to maintain the states of the first controlled switch and the second controlled switch during a power loss without requiring the states of the first controlled switch and the second controlled switch to be reprogrammed after power is restored; and A second circuit, responsive to a decoding signal delivered by the generator over said two-wire line, for controlling the first circuit according to said decoding signal to set said first and second controlled switches to a corresponding particular electrode configuration associated with said decoding signal, and means for previously programming the state of the first and second non-volatile programmable memory components by corresponding decoding signals applied by the generator on the two-wire line.

2. The module of claim 1, wherein the first and second controlled switches are complementary switches having a common control terminal, wherein a voltage applied to said common control terminal provides that one of the controlled switches is controlled open the other is controlled closed.

3. The module of claim 2, wherein said first and second non-volatile programmable memory components are connected in series between said minimum output of said MMG circuit and said maximum output of said MMG circuit, wherein one of the non-volatile programmable memory components is programmed into one of its stable states and the other non-volatile programmable memory components is programmed in the other of the stable states, and the midpoint of the series circuit being connected to said common control terminal.

4. The module of claim 1, wherein the non-volatile programmable memory component further comprises a suspended nanotube cell.

5. The module of claim 1, wherein the non-volatile programmable memory component further comprises a magnetic tunnel junction cell.

6. A multiple-electrode lead system for use with an implantable medical device, the lead system comprising:
a first wire and a second wire disposed within an elongated lead body;
a plurality of electrodes; and
a switching module configured to selectively couple one of the first wire and the second wire to at least one electrode of the plurality of electrodes, wherein the switching module comprises at least one switching device and at least one non-volatile programmable memory component;
wherein the at least one non-volatile programmable memory component is configured to maintain a current stable state from among at least two stable states of the at least one non-volatile programmable memory component in absence of a supply power to the at least one non-volatile programmable memory component;
wherein the current stable state of the at least one non-volatile programmable memory component is configured to determine a configuration of the at least one switching device, wherein the configuration is one of a first configuration in which the at least one electrode is connected to the first wire and a second configuration in which the at least one electrode is connected to the second wire;
wherein the switching module further comprises a control circuit configured to receive a control signal from a generator of the implantable medical device and control the current stable state of the at least one non-volatile programmable memory component based on the control signal;
wherein the implantable medical device is configured to use the control signal to control connection of the plurality of electrodes to one of the first wire and the second wire; and
wherein the at least one non-volatile programmable memory component is configured to maintain the configuration of the at least one switching device during a power loss without requiring the configuration to be reprogrammed after power is restored.

7. The lead system of claim 6, wherein the switching module comprises a maximum-minimum generator (MMG) circuit configured to receive a signal from the control circuit and to control the current stable state of the at least one non-volatile programmable memory component based on the signal.

8. The lead system of claim 7, wherein the at least one switching device comprises a first switching device and a second switching device, wherein the first and second switching devices are complementary switches having a common control terminal, and wherein a voltage applied to the common control terminal is configured to cause one of the controlled switches is to be in an open state and the other to be in a closed state.

9. The lead system of claim 8, wherein the at least one non-volatile programmable memory component comprises a first non-volatile programmable memory component and a second non-volatile programmable memory component, wherein the first and second non-volatile programmable memory components are connected in series between two outputs of the MMG circuit, wherein one of the non-volatile programmable memory components is programmed into a first stable state of the at least two stable states and the other non-volatile programmable memory component is programmed into a second stable state of the at least two stable states, and wherein a midpoint of the series circuit is connected to the common control terminal.

10. The lead system of claim 6, wherein the at least one non-volatile programmable memory component comprises a suspended nanotube cell.

11. The lead system of claim 6, wherein the at least one non-volatile programmable memory component comprises a magnetic tunnel junction cell.

12. A method of controlling connection of at least one electrode of a multiple-electrode lead of an implantable medical device to one of a first wire and a second wire of the lead, the method comprising:
providing a switching module comprising at least one switching device and at least one non-volatile programmable memory component, wherein the at least one non-volatile programmable memory component is configured to maintain a current stable state from among at least two stable states of the at least one non-volatile programmable memory component in absence of a supply power to the at least one non-volatile programmable memory component;
receiving a control signal from a generator of the implantable medical device;
selectively coupling the at least one electrode to one of the first wire and the second wire based on the control signal, wherein selectively coupling the at least one electrode to one of the first wire and the second wire comprises setting the current stable state based on the control signal, wherein setting the current stable state to a first stable state of the at least two stable states causes the at least one switching device to couple the at least one electrode to the first wire, and wherein setting the current stable state to a second stable state of the at least two stable states causes the at least one switching device to couple the at least one electrode to the first wire; and
maintaining, using the current stable state of the at least one non-volatile programmable memory component, a current configuration of the at least one switching device during a power loss without requiring the configuration to be to be reprogrammed after power is restored.

13. The method of claim 12, further comprising controlling the current stable state of the at least one non-volatile programmable memory component using a maximum-minimum generator (MMG) circuit.

14. The method of claim 13, wherein the at least one switching device comprises a first switching device and a second switching device, wherein the first and second switching devices are complementary switches having a common control terminal, and wherein a voltage applied to the common control terminal is configured to cause one of the controlled switches is to be in an open state and the other to be in a closed state.

15. The method of claim 14, wherein the at least one non-volatile programmable memory component comprises a first non-volatile programmable memory component and a second non-volatile programmable memory component, wherein the first and second non-volatile programmable memory components are connected in series between two outputs of the MMG circuit, wherein one of the non-volatile programmable memory components is programmed into a first stable state of the at least two stable states and the other non-volatile programmable memory component is programmed into a second stable state of the at least two stable states, and wherein a midpoint of the series circuit is connected to the common control terminal.

16. The method of claim 12, wherein the at least one non-volatile programmable memory component comprises a suspended nanotube cell.

17. The method of claim 12, wherein the at least one non-volatile programmable memory component comprises a magnetic tunnel junction cell.

\* \* \* \* \*